(12) United States Patent
Ein-Gal

(10) Patent No.: US 9,144,691 B2
(45) Date of Patent: Sep. 29, 2015

(54) OPTIMIZING INTENSITY MAPS FOR PLURAL ORIENTATIONS USING SEGMENTED RADIATION FIELDS

(71) Applicant: Moshe Ein-Gal, Ramat Hasharon (IL)

(72) Inventor: Moshe Ein-Gal, Ramat Hasharon (IL)

(*) Notice: Subject to any disclaimer, the term of this patent is extended or adjusted under 35 U.S.C. 154(b) by 157 days.

(21) Appl. No.: 13/656,752

(22) Filed: Oct. 22, 2012

(65) Prior Publication Data

US 2014/0110604 A1  Apr. 24, 2014

(51) Int. Cl.
*A61N 5/10* (2006.01)
*G21F 3/00* (2006.01)

(52) U.S. Cl.
CPC ............... *A61N 5/1042* (2013.01); *G21F 3/00* (2013.01); *A61N 5/1081* (2013.01); *A61N 2005/1095* (2013.01)

(58) Field of Classification Search
CPC ............... A61N 5/1031; A61N 5/103; A61N 2005/1032; A61N 5/1036; A61N 5/1047; A61N 5/1045; A61N 5/00
USPC ................... 250/492.3, 505.1, 491.1, 492.22; 378/65; 703/20
See application file for complete search history.

(56) References Cited

U.S. PATENT DOCUMENTS

| | | | |
|---|---|---|---|
| 5,596,619 A * | 1/1997 | Carol | 378/65 |
| 2005/0123098 A1* | 6/2005 | Wang et al. | 378/151 |
| 2006/0256915 A1* | 11/2006 | Otto et al. | 378/65 |
| 2009/0037145 A1* | 2/2009 | Suzuki et al. | 702/183 |
| 2010/0322381 A1* | 12/2010 | Stahl et al. | 378/65 |
| 2011/0081002 A1* | 4/2011 | Keall et al. | 378/65 |
| 2011/0211665 A1* | 9/2011 | Maurer et al. | 378/9 |

* cited by examiner

*Primary Examiner* — Brooke Purinton
(74) *Attorney, Agent, or Firm* — Dekel Patent Ltd.; David Klein

(57) ABSTRACT

A modulator for use in a radiation system with directional radiation beams respectively collimated into radiation fields, including a plurality of displaceable radiation attenuating elements arranged in at least one row, the radiation attenuating elements being configured to attenuate portions of a radiation beam inside the radiation field according the position of the radiation attenuating elements, and wherein each radiation attenuating element is respectively attached to a substantially radiolucent member, and a driver operable to store motion profiles and to respectively drive the radiation attenuating elements in directions generally perpendicular to the radiation beam via the substantially radiolucent members, wherein the respective motions of the radiation attenuating elements are according to corresponding motion profiles, and wherein a motion profile relates position and/or velocity of the radiation attenuating elements to time and/or irradiation level.

8 Claims, 2 Drawing Sheets

OPTIMIZING INTENSITY MAPS FOR PLURAL ORIENTATIONS USING SEGMENTED RADIATION FIELDS

FIELD OF THE INVENTION

The present invention relates generally to radiotherapy and irradiation systems, and particularly to modulating the intensity of a radiation beam by one or more attenuating leaves positioned in a radiation field.

BACKGROUND OF THE INVENTION

Medical equipment for radiation therapy treats tumorous tissue with high energy radiation. The dose and the placement of the dose must be accurately controlled to insure that the tumor receives sufficient radiation to be destroyed, and that damage to the surrounding and adjacent non-tumorous tissue, referred to as organs at risk (OAR), is minimized.

Radiation therapy typically uses a radiation source that is external to the patient, typically either a radioisotope, such as cobalt-60, or a high energy x-ray source, such as a linear accelerator. The external source produces a collimated beam directed into the patient to the tumor site. However, external-source radiation therapy undesirably irradiates a significant volume of OAR in the path of the radiation beam along with the tumorous tissue. The adverse effect of irradiation of healthy tissue may be reduced, while maintaining a given dose of radiation in the tumorous tissue, by projecting the external radiation beam into the patient at a variety of gantry angles with the beams converging on the tumor site. This reduces the total dose to the healthy tissue during the entire treatment.

The irradiation of healthy tissue also may be reduced by tightly collimating the radiation beam to the general cross section of the tumor taken perpendicular to the axis of the radiation beam. Numerous systems exist for producing such a circumferential collimation, such as systems with multileaf collimators. The multileaf collimator (MLC) may control the width and offset of the radiation beam as a function of gantry angle so that tumorous tissue may be accurately targeted.

Collimation is just one way of shaping the radiation beam. Additionally or alternatively, the radiation beam may be spatially attenuated. Collimators control the outline of the radiation beam; attenuators control the intensity of the radiation beams that are beamed at the tissue. Phrased more technically, collimators block radiation so as to create a generally binary spatial intensity distribution (binary: passed or blocked), while attenuators or beam modulators, typically produce continuous spatial modulation of the beam intensity by selective attenuation.

For example, intensity modulated radiotherapy (IMRT) is aimed at irradiating a target while protecting healthy tissue, especially organs-at-risk (OAR). Intensity modulation is implemented either by multileaf collimators or by attenuating modulators. A desired intensity map is approximated by segmentation: forming a sequence of aperture segments consecutively shaped by the MLC.

Using inverse planning for radiotherapy treatment, the physician prescribes desired target dose and tolerances for sensitive structures, and optimization software explores a multitude of possibilities to determine machine settings so as to closely deliver the prescribed radiation dose. Irradiation is delivered from a discrete set of orientations or from a continuous arc.

In order to modulate radiation beam intensity in a given field, the beam is conceptually partitioned into many small beam segments which are generically called pencil beams or beamlets. Beamlets are indexed by their respective positions in a radiation field and by the orientation of the beam relative to a patient. Dose distribution produced by a beamlet in the patient is calculated and/or measured. Optimizing IMRT amounts to selecting respective intensities of the beamlets, arranged as an intensity map, so as to achieve optimal accumulated dose distribution in the patient. Since separate irradiation of each beamlet is cumbersome, beamlets are grouped into field segments incorporating respectively uniform segment intensities. Successive irradiation of the segments approximates the optimized intensities prescribed by the intensity map. Direct methods optimize the field shape in addition to beamlets intensities, while delivery constraints may be incorporated in the optimization process.

Collimators are configured to define a radiation field by blocking substantially all radiation outside the field aperture. Typically, a desired radiation field is produced by cascaded collimators. Primary, secondary and tertiary collimators are termed according to their respective proximity to the radiation source. A fixed-size stationary primary collimator defines the maximal field size. Secondary collimators are movable and are operable to generally produce rectangular fields of variable size and location. Finer field shaping is further accomplished by tertiary collimators, typically conical (sometimes called cylindrical) collimators of various diameters or multi-leaf collimators. Successive cascaded collimators overlap so as to prevent radiation from leaking between collimators.

A multi-leaf collimator modifies field aperture by adjusting spaces between respective front-ends of opposing leaves. The produced field can be modified during irradiation or between irradiations. Respective rear-ends of MLC leaves overlap the secondary collimator (typically jaws).

While collimators block radiation outside a field, beam intensity can be modulated by a physical modulator covering the whole field. Such a modulator incorporates spatially variable attenuating properties tailored to a specific intensity map. Simple modulators, e.g., a wedge, do not generally provide on their own IMRT with sufficient quality.

SUMMARY OF THE INVENTION

The present invention seeks to provide a novel device and method for modulating intensity of a radiation beam in a radiation field by movable leaves configured to attenuate beam portions of the radiation field, as is described hereinbelow.

In accordance with an embodiment of the present invention, a multi-leaf modulator is provided for use in a radiation system that emits a radiation beam in a radiation field, the modulator including a plurality of displaceable leaves configured to attenuate portions of the radiation beam in the radiation field, and means for displacing the leaves by radiolucent members attached to the leaves. The displacement is according to respective motion profiles derived from an optimized attenuation map so as to obtain a desired dose distribution. The attenuation of a leaf in a given location is proportional to the dwelling time of the leaf in that location or it is inversely proportional to the speed of the leaf in that location.

It is noted that in the description, the members attached to the leaves are referred to as radiolucent. This term not only encompasses members that allow passage of the beam with substantially no attenuation, but also encompasses finite (small) attenuation, that is, significantly smaller than that of the leaf, such as no more than 10% of the leaf attenuation, more preferably no more than 5% of the leaf attenuation, and most preferably no more than 1% of the leaf attenuation. This small attenuation can be incorporated in the calculation of the leaf motion profile.

There is thus provided in accordance with an embodiment of the present invention a modulator for use in a radiation system, the radiation system being capable of irradiating a target from a plurality of orientations, wherein the orientations are associated with directional radiation beams respectively collimated into radiation fields, including a plurality of displaceable radiation attenuating elements arranged in at least one row, the radiation attenuating elements being configured to attenuate portions of a radiation beam inside the radiation field according the position of the radiation attenuating elements, and wherein each radiation attenuating element is respectively attached to a substantially radiolucent member, and a driver operable to store motion profiles and to respectively drive the radiation attenuating elements in directions generally perpendicular to the radiation beam via the substantially radiolucent members, wherein the respective motions of the radiation attenuating elements are according to corresponding motion profiles, and wherein a motion profile relates position and/or velocity of the radiation attenuating elements to time and/or irradiation level.

In one non-limiting embodiment, a collimator is operable to substantially block radiation outside a radiation field.

In one non-limiting embodiment, a radiation source is operable to produce a radiation beam toward a target.

In one non-limiting embodiment, a target positioner is provided for adjusting the relative position of the target and the radiation beam.

In one non-limiting embodiment, a modulator positioner is provided for adjusting the relative position of the modulator and the radiation beam.

In one non-limiting embodiment, an additional modulator is operable to modulate the radiation beam in the radiation field.

In one non-limiting embodiment, a processor is in communication with the driver, wherein the processor is operable to derive attenuation maps associated with irradiating the target from respective orientations and to transform an attenuation map into motion profiles of the radiation attenuating elements, wherein the attenuation map provides attenuation levels related to the radiation attenuating elements in respective positions.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
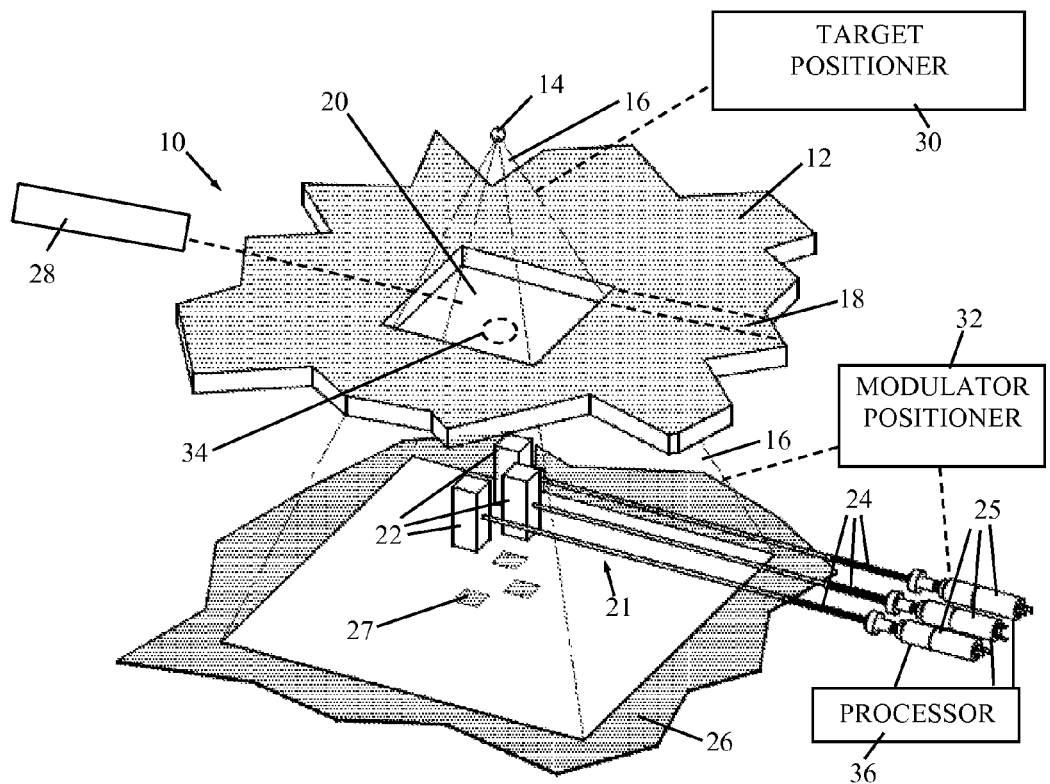
FIG. 1 is a simplified pictorial illustration of an irradiation system and modulator system, constructed and operative in accordance with an embodiment of the present invention.

Reference is now made to FIG. 1, which illustrates a radiation system 10 with a collimator system 12 (or for short, collimator 12), constructed and operative in accordance with a non-limiting embodiment of the present invention.

In the non-limiting illustrated embodiment, radiation system 10 (e.g., a LINAC) includes a radiation source 14 that emits a radiation beam 16. The radiation source 14 and collimator 12 can be positioned in a gantry (not shown), as is well known in the art. Any radiation may be used, such as but not limited to, electron radiation or photon radiation (gamma radiation). As is known in the art, during treatment, beam 16 is trained on a target typically surrounding the isocenter of the gantry rotation. Imaging apparatus (not shown), such as a fluoroscope or ultrasound apparatus, for example, may be provided for imaging the target irradiated by radiation beam 16. The imaging apparatus may be used in conjunction with a closed loop, feedback control system (not shown) for controlling a relative position between the target and the radiation beam and for controlling the functioning of collimator 12.

Collimator 12 is arranged to form an aperture 20 through which radiation beam 16 can pass. In one embodiment, collimator 12 is a single custom made radiation block shaped in accordance with previously acquired data of the tumor in the patient. In another embodiment of the present invention, collimator 12 may be a multileaf collimator including a plurality of movable radiation blocking leaves 18 arranged to form aperture 20. In general, although not limited by this, aperture 20 has a closed perimeter defined by the radiation block or by the leaves 18.

Radiation system 10 is thus capable of irradiating a target from a plurality of orientations, wherein the orientations are associated with directional radiation beams 16 respectively collimated by collimator 12 into radiation fields.

Figure 2:
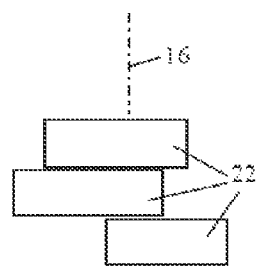
FIG. 2 is a simplified pictorial illustration of an arrangement of radiation attenuating elements, constructed and operative in accordance with an alternative embodiment of the present invention.

In accordance with an embodiment of the present invention, a multileaf modulator 21 is provided for use with radiation system 10. The multileaf modulator 21 includes one or more radiation attenuating elements 22, which are positioned to block a portion of radiation beam 16 that passes through a field of view of aperture 20. In the illustrated embodiment of FIG. 1, three radiation attenuating elements 22 are shown. FIG. 2 shows an alternative embodiment, wherein a plurality of radiation attenuating elements 22 are arranged to move along different planes substantially perpendicular to radiation beam 16. The radiation attenuating elements 22 may be a plurality of displaceable leaves arranged in at least one row. The leaves are configured to attenuate portions of radiation beam 16 inside the radiation field according the position of the leaves.

Radiation attenuating element 22 is disposed on (attached to, joined to, or extending from) a substantially radiolucent member 24 that is made of a material that does not substantially block radiation beam 16. The one or more radiation attenuating elements 22 are moved by a driver 25 (e.g., linear actuator, step motor and others) to different positions in the field of view of aperture 20. In one embodiment, driver 25 stores motion profiles and respectively drives radiation attenuating elements 22 (also referred to as leaves 22) in directions generally perpendicular to the radiation beam 16 via the substantially radiolucent members 24. The respective motions of the leaves 22 are according to corresponding motion profiles; the motion profile relates position and/or velocity of the radiation attenuating element 22 to time and/or irradiation level.

Radiation attenuating element 22 attenuates a portion of radiation beam 16 that passes through aperture 20, but other portions of radiation beam 16 outside of radiation attenuating element 22 pass substantially un-attenuated through aperture 20 and radiolucent member 24. (In the case of complete attenuation, radiation attenuating element 22 completely blocks the portion of radiation beam 16.) Thus, as seen in a plane 26 perpendicular to the beam direction, radiation passes all around radiation attenuating element 22 in aperture 20 but not at the position of radiation attenuating element 22. The shadow 27 of radiation attenuating element 22 is clearly seen on plane 26.

In the illustrated embodiment, radiation attenuating element 22 and radiolucent member 24 are not coplanar with the one or more leaves 18. However, in another non-limiting embodiment shown in broken lines in FIG. 1, radiation attenuating element 22 and radiolucent member 24 may be coplanar with at least some of the leaves 18.

The collimator may further include apparatus 28 for determining position and shape of the aperture (e.g., a camera).

A target positioner 30 (such as a gantry) may be provided for adjusting the relative position of the target and radiation beam 16. A modulator positioner 32 may be provided for adjusting the relative position of the modulator 21 and radiation beam 16. For example, modulator 21 may be mounted on a precisely movable table. As another example, modulator positioner 32 may be the gantry. An additional modulator 34 (e.g., an additional attenuator) may be provided to modulate radiation beam 16 in the radiation field.

A processor 36 may be in communication with driver 25. Processor 36 is operable to derive attenuation maps associated with irradiating the target from respective orientations and to transform an attenuation map into motion profiles of the radiation attenuating elements 22, wherein the attenuation map provides attenuation levels related to the radiation attenuating elements 22 in respective positions.

Figure 3:
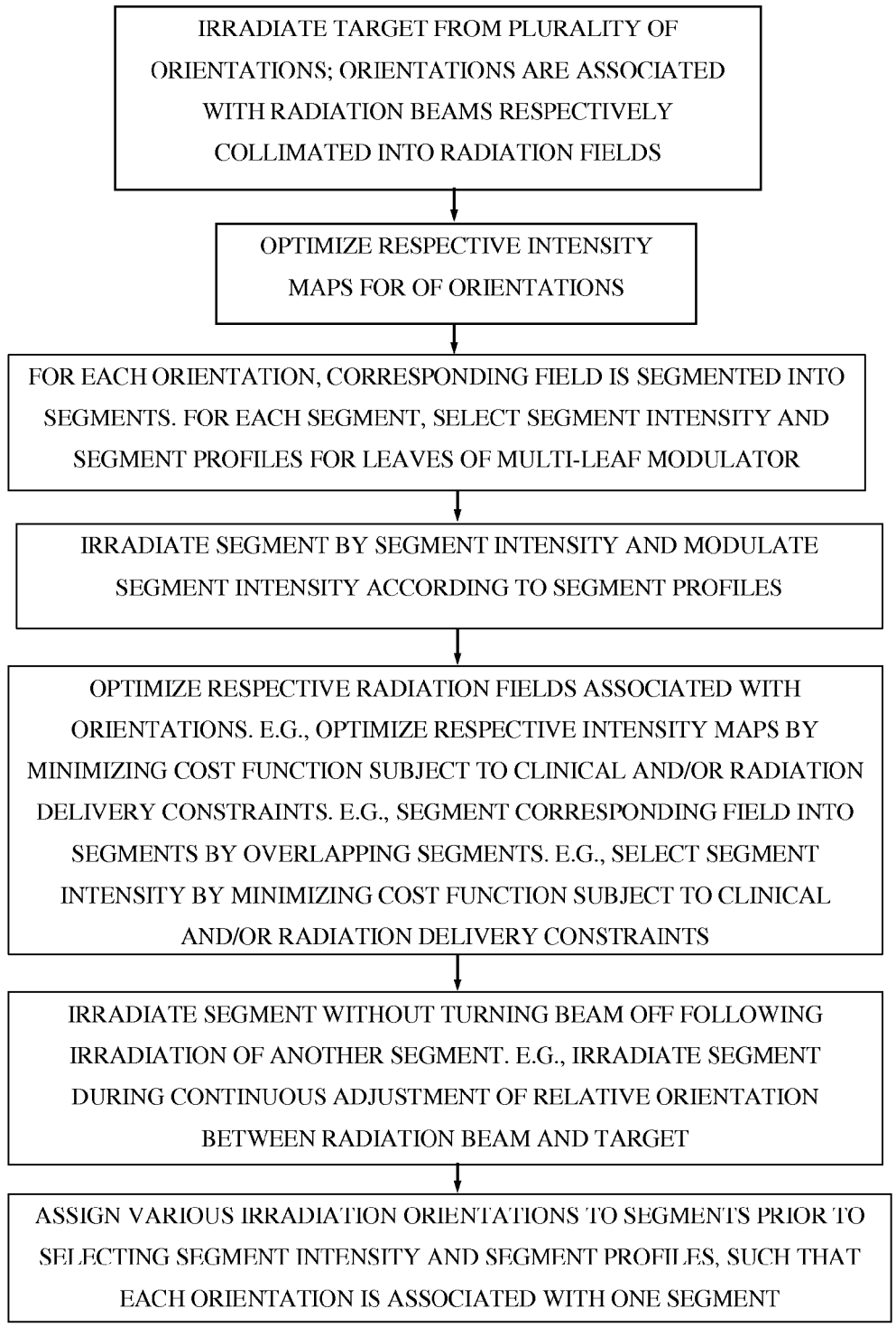
FIG. 3 is a simplified flow chart of method for performing IMRT, in accordance with an embodiment of the present invention.

Reference is now made to FIG. 3, which illustrates one non-limiting example of a method for performing IMRT, such as controlled by processor 36, in accordance with an embodiment of the present invention. The method includes irradiating a target from a plurality of orientations, wherein the orientations are associated with radiation beams respectively collimated into radiation fields. Respective intensity maps are optimized for the plurality of orientations.

For each orientation, the corresponding field is segmented into segments, and for each segment, segment intensity and segment profiles are selected for the leaves of the multi-leaf modulator. A segment profile relates position and/or velocity of a leaf to time and/or irradiation level. The segment is irradiated by the segment intensity and the segment intensity is modulated according to the segment profiles.

The method may further include optimizing the respective radiation fields associated with the orientations. For example, optimizing respective intensity maps may include minimizing a cost function subject to clinical and/or radiation delivery constraints. Segmenting the corresponding field into segments may include overlapping segments. Selecting segment intensity may be done by minimizing a cost function subject to clinical and/or radiation delivery constraints.

The segment may be irradiated without turning the beam off following irradiation of another segment. The segment may be irradiated during a continuous adjustment of the relative orientation between the radiation beam and the target.

The method may further include assigning various irradiation orientations to the segments prior to selecting segment intensity and segment profiles, such that each orientation is associated with one segment.

The scope of the present invention includes both combinations and subcombinations of the features described hereinabove as well as modifications and variations thereof which would occur to a person of skill in the art upon reading the foregoing description and which are not in the prior art.

What is claimed is:

1. A method for use in intensity modulated radiation therapy by irradiating a target from a plurality of orientations, wherein the orientations are associated with radiation beams respectively collimated into radiation fields, comprising the steps of:

for each of the plurality of orientations, segmenting the corresponding radiation field into segments, and for each segment:

selecting segment intensity and segment profiles for radiation attenuating elements of a modulator, and irradiating the segment by the segment intensity and modulating the segment intensity according to the segment profiles;

and wherein said modulator comprises a plurality of solid, displaceable radiation attenuating elements arranged in at least one row, said radiation attenuating elements being configured to attenuate portions of a radiation beam inside the radiation field according to the position of the radiation attenuating elements, and wherein each radiation attenuating element is respectively attached to a substantially radiolucent member; and wherein the step of modulating the segment intensity according to the segment profiles comprises storing motion profiles and driving said radiation attenuating elements in directions generally perpendicular to the radiation beam via the substantially radiolucent members, wherein the respective motions of the radiation attenuating elements are according to corresponding motion profiles, and wherein a motion profile of each segment relates position and/or velocity of said radiation attenuating elements to time and/or irradiation level.

2. The method according to claim 1, further comprising optimizing the respective radiation fields associated with the orientations.

3. The method according to claim 1, further comprising minimizing a cost function subject to clinical and/or radiation delivery constraints.

4. The method according to claim 1, wherein segmenting the corresponding field into segments comprises overlapping segments.

5. The method according to claim 1, wherein selecting segment intensity is by minimizing a cost function subject to clinical and/or radiation delivery constraints.

6. The method according to claim 1, wherein a segment is irradiated without turning the beam off following irradiation of another segment.

7. The method according to claim 1, wherein irradiating a segment is executed during a continuous adjustment of the relative orientation between the radiation beam and the target.

8. The method according to claim 1, further incorporating assigning various irradiation orientations to the segments prior to selecting segment intensity and segment profiles, such that each orientation is associated with one segment.

* * * * *